United States Patent
Zucker et al.

(10) Patent No.: US 12,133,807 B2
(45) Date of Patent: Nov. 5, 2024

(54) INTERBODY TOOL, SYSTEMS, AND METHODS

(71) Applicant: MAZOR ROBOTICS LTD., Caesarea (IL)

(72) Inventors: Ido Zucker, Tel Aviv (IL); Arik Levy, Herzliya (IL)

(73) Assignee: MAZOR ROBOTICS LTD., Caesarea (IL)

(*) Notice: Subject to any disclaimer, the term of this patent is extended or adjusted under 35 U.S.C. 154(b) by 0 days.

(21) Appl. No.: 17/897,628

(22) Filed: Aug. 29, 2022

(65) Prior Publication Data
US 2022/0409400 A1  Dec. 29, 2022

Related U.S. Application Data

(62) Division of application No. 16/927,548, filed on Jul. 13, 2020, now abandoned.

(51) Int. Cl.
*A61F 2/46* (2006.01)
*A61F 2/30* (2006.01)
*A61F 2/44* (2006.01)

(52) U.S. Cl.
CPC ............ *A61F 2/4611* (2013.01); *A61F 2/442* (2013.01); *A61F 2002/30156* (2013.01); *A61F 2002/30266* (2013.01); *A61F 2002/3055* (2013.01); *A61F 2002/4632* (2013.01); *A61F 2002/4658* (2013.01); *A61F 2002/4666* (2013.01); *A61F 2002/4693* (2013.01)

(58) Field of Classification Search
CPC ........ A61F 2/4611; A61F 2/30; A61F 2/4684; A61F 2002/4658; A61F 2002/4666; A61F 2002/4668; A61F 2002/469; A61F 2002/4693; A61F 2002/4694
See application file for complete search history.

(56) References Cited

U.S. PATENT DOCUMENTS

| | | | |
|---|---|---|---|
| 7,542,791 B2 | 6/2009 | Mire et al. | |
| 8,105,382 B2 | 1/2012 | Olmos et al. | |
| 8,317,798 B2 | 11/2012 | Lim et al. | |

(Continued)

FOREIGN PATENT DOCUMENTS

| | | |
|---|---|---|
| DE | 60225150 | 2/2009 |
| WO | WO 2005/006944 | 1/2005 |

OTHER PUBLICATIONS

Stewart "A Platform with Six Degrees of Freedom," Proceedings of the Institution of Mechanical Engineers, Jun. 1965, vol. 180, No. 1, pp. 371-386.

(Continued)

*Primary Examiner* — Matthew J Lawson
(74) *Attorney, Agent, or Firm* — Sheridan Ross P.C.

(57) ABSTRACT

An interbody tool may include an upper portion with an upper contact surface and a plurality of upper legs; a lower portion with a lower contact surface and a plurality of lower legs, each of the lower legs movably connected to one of the upper legs; a plurality of gauges, each gauge configured to measure a position of one of the plurality of upper legs relative to a corresponding one of the plurality of lower legs; at least one actuator configured to selectively push the upper portion away from the lower portion; and at least one sensor for measuring a force exerted by the at least one actuator.

18 Claims, 5 Drawing Sheets

(56) References Cited

U.S. PATENT DOCUMENTS

| | | |
|---|---|---|
| 8,465,547 B2 | 6/2013 | Mellkent et al. |
| 9,186,259 B2 | 11/2015 | To et al. |
| 9,216,098 B2 | 12/2015 | Trudeau et al. |
| 9,386,975 B2 | 7/2016 | Markworth et al. |
| 9,883,951 B2 | 2/2018 | Lopez |
| 2004/0010259 A1 | 1/2004 | Keller et al. |
| 2006/0247657 A1 | 11/2006 | Trieu et al. |
| 2007/0050030 A1 | 3/2007 | Kim |
| 2007/0093901 A1 | 4/2007 | Grotz et al. |
| 2007/0161872 A1* | 7/2007 | Kelly .................. A61B 90/06 600/300 |
| 2007/0250172 A1 | 10/2007 | Moskowitz et al. |
| 2008/0167718 A1 | 7/2008 | Protopsaltis |
| 2009/0234456 A1 | 9/2009 | Nycz |
| 2010/0010494 A1 | 1/2010 | Quirno |
| 2010/0057204 A1* | 3/2010 | Kadaba .................. A61F 2/44 623/17.12 |
| 2010/0262160 A1* | 10/2010 | Boyden ................ A61B 17/68 600/301 |
| 2011/0257655 A1* | 10/2011 | Copf, Jr. .................. A61F 2/46 606/90 |
| 2013/0079680 A1 | 3/2013 | Stein et al. |
| 2015/0105782 A1 | 4/2015 | D'Lima et al. |
| 2018/0177612 A1 | 6/2018 | Trabish et al. |
| 2019/0247200 A1 | 8/2019 | Ulrich, Jr. et al. |
| 2021/0038408 A1* | 2/2021 | Permeswaran ....... A61F 2/4611 |
| 2021/0393337 A1 | 12/2021 | Zucker |
| 2022/0008221 A1 | 1/2022 | Zucker et al. |

OTHER PUBLICATIONS

International Search Report and Written Opinion for International (PCT) Patent Application No. PCT/US2021/036909, dated Sep. 28, 2021, 12 pages.

Official Action for U.S. Appl. No. 16/927,548, dated Nov. 4, 2021 6 pages Restriction Requirement.

Official Action for U.S. Appl. No. 16/927,548, dated Jan. 28, 2022 15 pages.

Official Action for U.S. Appl. No. 16/927,548, dated May 2, 2022 14 pages.

* cited by examiner

INTERBODY TOOL, SYSTEMS, AND METHODS

CROSS REFERENCE TO RELATED APPLICATIONS

This application is a division of U.S. patent application Ser. No. 16/927,548, filed on Jul. 13, 2020, and entitled "Interbody Tool, Systems, and Methods," which application is incorporated herein by reference in its entirety.

FIELD

The present technology generally relates to surgical tools, and more particularly relates to surgical tools for measuring one or more anatomical dimensions during surgery.

BACKGROUND

Various surgical procedures involve the use of one or more tools for transmitting torque, whether for drilling, tapping, inserting a screw, or otherwise. Surgical robots are useful for holding and/or operating one or more tools or devices during a surgery, and may operate autonomously (e.g., without any human input during operation), semi-autonomously (e.g., with some human input during operation), or non-autonomously (e.g., only as directed by human input).

SUMMARY

An interbody tool according to one embodiment of the present disclosure comprises: an upper portion comprising an upper contact surface and a plurality of upper legs; a lower portion comprising a lower contact surface and a plurality of lower legs, each of the lower legs movably connected to one of the upper legs; a plurality of gauges, each gauge configured to measure a position of one of the plurality of upper legs relative to a corresponding one of the plurality of lower legs; at least one actuator configured to selectively push the upper portion away from the lower portion; and at least one sensor for measuring a force exerted by the at least one actuator.

The plurality of upper legs may comprise three upper legs. Each of the plurality of upper legs may be connected to the upper portion via a joint. Each of the plurality of gauges may be an encoder. The at least one actuator may be configured to selectively adjust a distance between the upper contact surface and the lower contact surface from about 6 mm to about 18 mm. The at least one actuator may comprise a hydraulic actuator, and the at least one sensor may comprise a pressure sensor. The at least one actuator may comprise a plurality of independently operable hydraulic actuators and the at least one sensor may comprise a plurality of pressure sensors. At least the plurality of upper legs, the plurality of lower legs, and the plurality of gauges may be contained within a housing.

The interbody tool may further comprise: a processor; and a memory. The memory may store instructions for execution by the processor, that, when executed, cause the processor to deactivate the at least one actuator when the force, as measured by the at least one sensor, reaches a predetermined threshold. The at least one actuator may comprise a plurality of actuators, each positioned proximate one of the plurality of upper legs and a corresponding one of the plurality of lower legs. The at least one actuator may comprise a scissor jack.

A method of measuring an interbody space according to another embodiment of the present disclosure comprises: inserting an interbody tool having an upper contact surface and a lower contact surface into an interbody space; activating at least one actuator of the interbody tool to expand a distance between the upper contact surface and the lower contact surface; monitoring, with a sensor, a characteristic of the at least one actuator; deactivating the at least one actuator when the characteristic reaches a predetermined threshold; and receiving information from a plurality of gauges positioned at a plurality of points between the upper contact surface and the lower contact surface about a distance between the upper contact surface and the lower contact surface at each of the plurality of points.

The at least one actuator may comprise a hydraulic actuator, and the characteristic may comprise a hydraulic pressure. The inserting may comprise causing a robotic arm to insert the interbody tool into the interbody space. The method may further comprise: selecting an interbody implant based on the received information; and inserting the selected interbody implant into the interbody space using the robotic arm. The at least one actuator may be configured to selectively adjust a distance between the upper contact surface and the lower contact surface at each of the plurality of points. The interbody space may be positioned between two vertebrae of a spine, and the activating may cause a change in at least one of a coronal alignment or a sagittal alignment of the spine.

An interbody measurement system according to another embodiment of the comprises: an interbody tool; at least one processor; and at least one memory. The interbody tool comprises: an upper portion comprising an upper contact surface; a lower portion comprising a lower contact surface; at least one actuator configured to selectively adjust a distance between the upper contact surface and the lower contact surface; and at least one sensor for measuring a characteristic of the at least one actuator. The at least one memory stores instructions for execution by the at least one processor that, when executed, cause the at least one processor to: receive data corresponding to the characteristic from the at least one sensor; and determine whether to de-activate the at least one actuator based on the data.

The interbody tool may further comprise a plurality of gauges positioned at a plurality of points between the upper contact surface and the lower contact surface. The at least one memory may store additional instructions for execution by the processor that, when executed, further cause the processor to receive, from the plurality of gauges, information about a distance between the upper contact surface and the lower contact surface at each of the plurality of points. The at least one memory may store additional instructions for execution by the processor that, when executed, further cause the processor to: select an implant based on the information about the distance between the upper contact surface and the lower contact surface at each of the plurality of points; and update a global alignment plan based on the selected implant.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
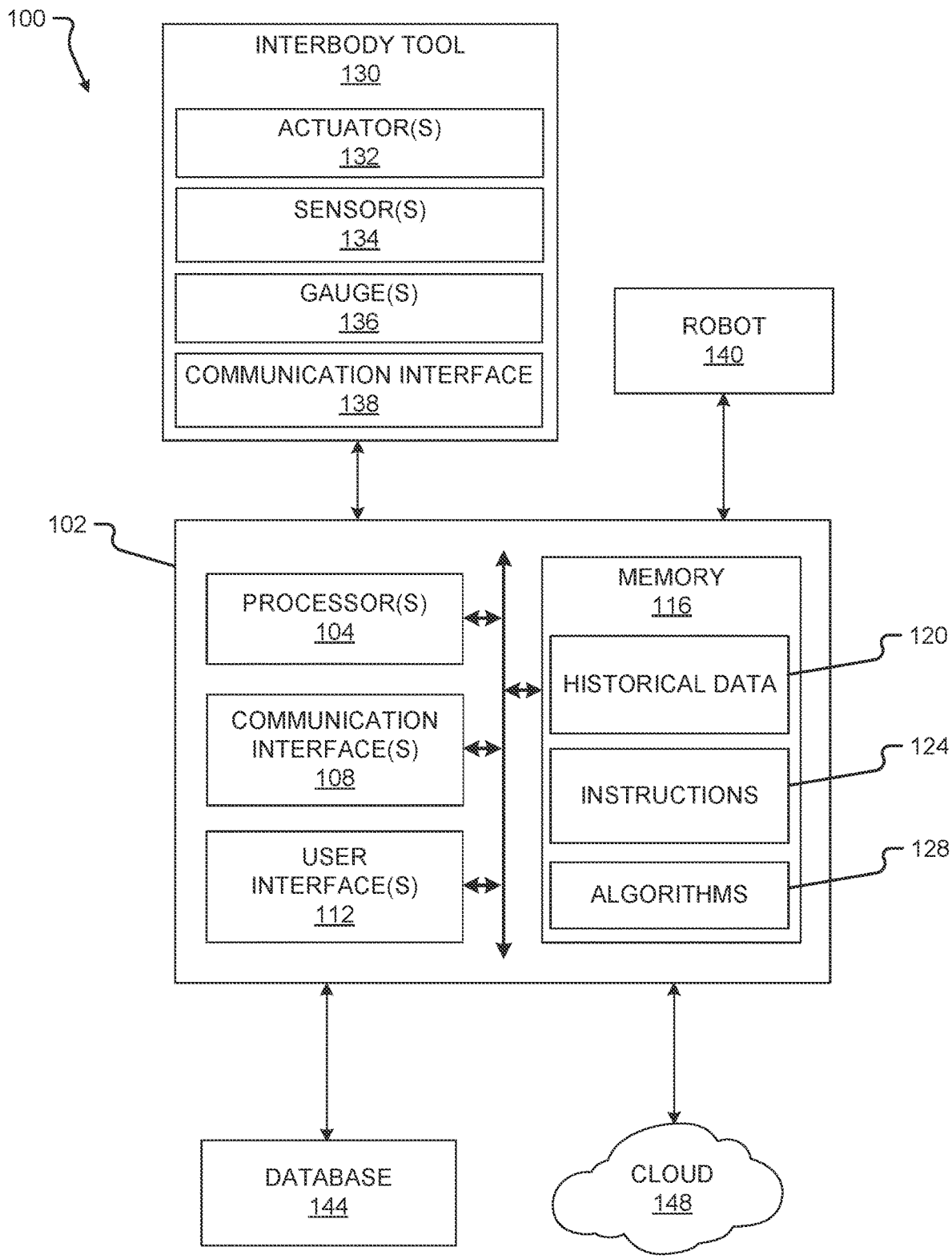
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Insertion of an interbody implant in a spine procedure may be done manually in the operating room by the surgeon. After clearing a path for the tools and removing the disc and cartilage covering the vertebrae, the surgeon will insert trials with interchangeable sizes to gauge the appropriate height for the interbody. This action is done manually and the feedback is subjective, based on the surgeon's "feel."

Embodiments of the present disclosure include an interbody tool that can be inserted into a clean disc space, expanded, and used to gauge the height of the of the interbody implant to be inserted. The height can be gauged at just one point or at a plurality of points. The tool may, in some embodiments, comprise a pressure sensor that allows the system to know when it is has reached a maximum or a predetermined threshold pressure. The height of the tool may then be determined and used to select an interbody implant.

The tool may have the ability to assume, fit, or match different profiles of interbody implants with non-uniform height to restore the interbody space between the vertebrae. The tool may record measurements in multiple dimensions, including lateral or sagittal rotation (pan), coronal rotation (tilt), and height. The tool may be inserted into the interbody space and expanded or otherwise configured to match the desired profile so as to determine whether the intended profile will achieve the desired purpose (e.g., to restore lordosis to the spine).

The tool may expand using one or more internal actuators (e.g., a motor-driven scissor jack), or may comprise one or more inflatable balloons operatively connected to an external pump (e.g., a pneumatic pump, a hydraulic pump). In some embodiments, the one or more internal actuators may be capable of providing height or other measurement information, while in other embodiments, one or more separate gauges (e.g., expandable encoders) may be used to measure or otherwise determine a height of the interbody tool at one or more points thereof.

Where a surgical robot is utilized to carry out a given interbody procedure autonomously (e.g., with no human intervention), information obtained using an interbody tool as described herein may be used to objectively determine an appropriately sized and shaped interbody implant for insertion by the surgical robot. Where a surgical plan specifies a particular interbody implant for insertion, one or more decision-making criteria may be applied to determine whether to change the plan (e.g., to increase or decrease the size of the implant, or to select an implant having a different profile) based on information obtained using the interbody tool.

Embodiments of the present disclosure may utilize machine learning to identify, from historical data regarding a plurality of interbody procedures, including a maximum pressure or force exerted by the interbody tool, size and profile information gathered from the interbody tool, the selected interbody implant, patient information (including, for example, spinal parameters of the patient), and associated patient outcomes (which may be measured or otherwise evaluated immediately, one year, five years, ten years, twenty years, and/or at any other interval following the procedures in question), one or more criteria, thresholds, and/or other parameters for use in connection with the present disclosure to improve chances of a positive outcome.

The present disclosure solves several technical problems, including but not limited to (1) a surgical robot used for interbody implant insertion procedures, while beneficial in terms of its ability to reduce the workload of a surgeon and ensure repeatability, is unable to gather the same type or level of tactile feedback, or make the same kinds of subjective judgments, regarding whether a given interbody implant is properly sized and has the proper shape, which could lead to potentially harmful or negative consequences for the patient; (2) that a surgical robot carrying out interbody implant insertion procedure autonomously cannot rely on a surgeon to provide input regarding a proper implant size and profile, whether based on the surgeon's subject implant or otherwise; and (3) that a preoperative or other surgical plan may not reflect important information obtained during an interbody implant insertion procedure (including during a trial portion of the procedure), and thus may need to be updated intraoperatively (and possibly autonomously) to ensure that the plan as ultimately executed accomplishes the intended purpose(s) thereof.

Turning now to FIG. 1, a block diagram of a system 100 according to at least one embodiment of the present disclosure is shown. The system 100 may be used, for example, to carry out an interbody implant insertion procedure, or to gather information relevant to such a procedure; to carry out one or more aspects of one or more of the methods disclosed herein; to improve patient outcomes in connection with a interbody implant insertion procedure or other surgical task or procedure; or for any other useful purpose. The system 100 comprises a computing device 102, an interbody tool 130, a robot 140, a database 144, and a cloud 148. Notwithstanding the foregoing, systems according to other embodiments of the present disclosure may omit any one or more of the robot 140, database 144, and/or the cloud 148. Additionally, systems according to other embodiments of the present disclosure may arrange one or more components of the system 100 differently (e.g., the interbody tool 130 may comprise one or more of the components of the computing device 102, and/or vice versa).

The computing device 102 comprises at least one processor 104, at least one communication interface 108, at least one user interface 112, and at least one memory 116. A computing device according to other embodiments of the present disclosure may omit one or both of the communication interface(s) 108 and/or the user interface(s) 112.

The at least one processor 104 of the computing device 102 may be any processor identified or described herein or any similar processor. The at least one processor 104 may be configured to execute instructions 124 stored in the at least one memory 116, which instructions 124 may cause the at least one processor 104 to carry out one or more computing steps utilizing or based on data received, for example, from the interbody tool 130, the robot 140, the database 144, and/or the cloud 148, and/or stored in the memory 116 (e.g., historical data 120). The instructions 124 may also cause the at least one processor 104 to utilize one or more algorithms 128 stored in the memory 116. In some embodiments, the at least one processor 104 may be used to control the interbody tool 130 and/or the robot 140 during a surgical procedure, including during an interbody implant insertion procedure or other procedure being carried out autonomously or semi-autonomously by the robot 140 using the interbody tool 130.

The computing device 102 may also comprise at least one communication interface 108. The at least one communication interface 108 may be used for receiving sensor data (e.g., from the interbody tool 130), a surgical plan or other planning data, or other information from an external source (such as the interbody tool 130, the robot 140, the database 144, the cloud 148, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the interbody tool 130, the robot 140, the database 144, the cloud 148, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102, the interbody tool 130, the robot 140, and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the method 500 described herein. The at least one memory 116 may store, for example, historical data 120, instructions 124, and/or algorithms 128. In some embodiments, the memory 116 may also store one or more preoperative and/or other surgical plans; one or more images of one or more patients, including in particular of an anatomical feature of the one or more patients on which one or more surgical procedures is/are to be performed; data received from the interbody tool 130 (including any component thereof) or elsewhere; and/or other information useful in connection with the present disclosure.

The historical data 120 may comprise data about a plurality of surgical procedures previously carried out and involving an interbody insertion procedure. The historical data 120 may comprise information about each such procedure (e.g., date and time of the procedure, anatomical location of the procedure, type of procedure, original surgical plan for the procedure, actual (e.g., as-executed) surgical plan for the procedure); information about the patient on whom the procedure was performed (e.g., patient age, gender, height, weight, relevant health information, position during procedure); data gathered during the procedure (e.g., parameters of the interbody space, data gathered using the interbody tool 130); and/or outcome data (e.g., implant status over time, fusion rates, degree of success in achieving any desired anatomical correction (e.g., correction of spinal kyphosis or lordosis), levels of pain (if any) experienced by the patient over time). In some embodiments, the historical data 120 may be used by a machine learning engine (which may comprise one or more of the algorithms 128) to identify correlations between or among, on the one hand, one or more of the data gathered from an interbody tool during a procedure, and on the other hand, one or more procedure outcomes, so as to yield one or more thresholds, criteria, or algorithms, and/or other parameters that can be utilized during a surgical procedure to increase the likelihood of a positive procedural outcome.

The instructions 124, as described above, may be or comprise any instructions for execution by the at least one processor 104 that cause the at least one processor to carry out one or more steps of any of the methods described herein. The instructions 124 may be or comprise instructions for carrying out an interbody implant insertion procedure, including instructions for using an interbody tool as described herein in connection such a procedure. The instructions 124 may additionally or alternatively enable the at least one processor 104, and/or the computing device 102 more generally, to operate as a machine learning engine that receives historical data 120 and outputs one or more thresholds, criteria, algorithms, and/or other parameters that can be utilized during an interbody implant insertion procedure, and/or during any other surgical procedure in which information obtained from an interbody tool as described herein may be relevant, to increase the likelihood of a positive procedural outcome.

The algorithms 128 may be or comprise any algorithms useful for converting sensor data received from the sensor(s) 134 and/or from the gauge(s) 136 into meaningful information (e.g., a calculated force value, pressure value, distance measurement). The algorithms 128 may further be or comprise any algorithms useful for generating one or more recommendations to a surgeon or other user of the system 100 based on information received from a sensor 134 and/or a gauge 136, and/or for modifying a preoperative or other surgical plan based on such information and/or an evaluation of such information. The algorithms 128 may further be or comprise algorithms useful for controlling the interbody tool 130 and/or the robot 140. In some embodiments, the algorithms 128 may be or include machine learning algorithms useful for analyzing the historical data 120.

The interbody tool 130 comprises one or more actuators 132, one or more sensors 134, one or more gauges 136, and a communication interface 138. The interbody tool 130 is adapted for insertion into an interbody space. Once inside the interbody space, the one or more actuators 132 are activated and cause the interbody tool 130 to expand against the upper and lower vertebrae that define the interbody space. In some embodiments, the interbody tool 130 comprises a scissor jack actuator. The scissor jack actuator may be operably connected to a motor and controlled by a processor such as the processor 104 (or a dedicated processor of the interbody tool 130), or the scissor jack actuator may be manually operable. In some embodiments, the one or more actuators 132 comprise a mechanical actuator other than a scissor jack actuator. Also in some embodiments, the one or more actuators 132 comprise a pneumatic or a hydraulic actuator. For example, an inflatable balloon may be positioned between an upper portion and a lower portion of the interbody tool 130, and inflated using an external pneumatic or hydraulic pump. Such an inflatable balloon may be made, for example, from a rubber-based or silicon-based material. Alternatively, one or more pneumatic or hydraulic cylinders may be provided between an upper portion and a lower portion of the interbody tool 130, and selectively operating using an external pneumatic or hydraulic pump, respectively. In still other embodiments, the one or more actuators 132 may comprise one or more electromagnets, and may utilize electromagnetic force to control a distance between an upper portion and a lower portion of the interbody tool 130. The one or more actuators 132 may be the same as or similar to any other actuators described herein.

The one or more actuators 132 may be configured to adjust a distance between an upper contact surface and a lower contact surface of the interbody tool 130 from a minimum amount of about six millimeters, or about four millimeters, or about two millimeters, to a maximum amount of about eighteen millimeters, or about twenty millimeters, or about twenty-two millimeters.

The one or more sensors 134 are used to measure a force or pressure exerted by the interbody tool 130 on the vertebrae (or to measure a force or pressure exerted by the one or more actuators 132 on the upper and lower portions of the interbody tool 130), so as to ensure that the force or pressure does not exceed a predetermined threshold. The predetermined threshold may be a safety threshold (e.g., to prevent the interbody tool 130 from damaging the vertebrae or otherwise harming the patient). In some embodiments, the predetermined threshold may be a patient characteristic (e.g., when a desired movement of the spine has been accomplished). The predetermined threshold may also be a threshold selected to prevent damage to the interbody tool 130. In some embodiments, the predetermined threshold may comprise a plurality of thresholds. The one or more actuators 132 may be deactivated (whether manually, automatically, or otherwise) when the predetermined threshold (or when at least one of a plurality of predetermined thresholds) is met. The one or more sensors 134 may be the same as or similar to any other sensors described herein.

The one or more sensors 134 may be operably connected to the one or more actuators 132. For example, where the actuator 132 is an inflatable balloon operably connected to a hydraulic pump, the one or more sensors 134 may comprise a pressure sensor configured to measure and/or determine a pressure of the hydraulic fluid within the inflatable balloon or elsewhere in the hydraulic circuit. In some embodiments, the one or more sensors 134 may comprise a sensor positioned in between an actuator 132 and an upper or lower portion or housing of the interbody tool 130, so as to measure a force or pressure exerted by the actuator 132 on the upper or lower portion or housing of the interbody tool 130. In still other embodiments, the one or more sensors 134 may comprise a sensor positioned on an upper and/or a lower contact surface of the interbody tool 130, so as to measure a force or pressure exerted by the interbody tool 130 on a vertebra against which the contact surface is positioned. The one or more sensors 134 may be in any suitable position to measure a force or pressure exerted by the interbody tool 130 on the anatomy that defines (in whole or in part) the interbody space in which the interbody tool 130 is positioned.

Whether during activation of the at least one actuator 132 or after deactivation thereof, the one or more gauges 136 may be used to measure a distance between an upper surface of the interbody tool 130 (proximate the vertebra defining the upper bound of the interbody space) and a lower surface of the interbody tool 130 (proximate the vertebra defining the lower bound of the interbody space). Where a plurality of gauges 136 are present, the gauges may be used to measure a distance between an upper surface of the interbody tool 130 and a lower surface thereof at a plurality of points. In such embodiments, the shape of the interbody space may be more accurately determined than in embodiments of the interbody tool 130 that utilize only one gauge 136. The one or more gauges may be or comprise linear encoders, optical distance sensors, or any other suitable sensors for measuring distances at a millimeter or finer resolution. The one or more gauges may be the same as or similar to any other gauges described herein.

The communication interface 138 may be the same as or similar to the communication interface 108. For example, the communication interface 138 may be utilized for receiving operating instructions and/or control signals from an external source (such as the computing device 102, the robot 140), and/or for transmitting data (e.g., corresponding to one or more measurements made by the gauge(s) 136) or other information to an external system or device (e.g., the computing device 102, the robot 140, the database 144, the cloud 148, and/or a portable storage medium (e.g., a USB drive, a DVD, a CD)). The communication interface 138 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the communication interface 138 may be useful for enabling the device 102 to communicate with one or more other processors 104 or computing devices 102, whether to reduce the time needed to accomplish a computing-intensive task or for any other reason.

In some embodiments, the system 100 may comprise more than one interbody tool 130.

The robot 140 may be any surgical robot or surgical robotic system. The robot 140 may be or comprise, for example, the Mazor X™ Stealth Edition robotic guidance system. The robot 140 may comprise a base that supports a robotic arm configured to hold the interbody tool 130. The robot 140 may comprise one or more robotic arms, each of which may be configured to hold the interbody tool 130. The robot 140 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure. The robot 140 may comprise one or more sensors useful for gathering information about where the robot or any portion thereof is positioned relative to a patient or, more specifically, relative to a patient's spine. The robot 140 may further comprise one or more sensors useful for assisting the robot 140 to determine whether it has good purchase and/or is positioned correctly.

The database 144 may store any information that is shown in FIG. 1 as being stored in the memory 116, including historical data such as the historical data 120, instructions such as the instructions 124, and/or algorithms such as the algorithms 128. In some embodiments, the database 144 stores one or more preoperative or other surgical plans. The database 144 may additionally or alternatively store, for example, information about or corresponding to one or more characteristics of the interbody tool 130, information about one or more available interbody implant sizes and/or profiles, and/or other information regarding available tools and/or equipment for use in connection with a surgical procedure. The database 144 may be configured to provide any such information to the computing device 102, the interbody tool 130, the robot 140, or to any other device of the system 100 or external to the system 100, whether directly or via the cloud 148. In some embodiments, the database 144 may be or comprise part of a hospital image storage system, such as a picture archiving and communication system (PACS), a health information system (HIS), and/or another system for collecting, storing, managing, and/or transmitting electronic medical records including image data. Also in some embodiments, the memory 116 may store any of the information described above.

The cloud 148 may be or represent the Internet or any other wide area network. The computing device 102 may be connected to the cloud 148 via the communication interface 108, using a wired connection, a wireless connection, or both. In some embodiments, the computing device 102 may communicate with the database 144 and/or an external device (e.g., a computing device) via the cloud 148.

Figure 2:
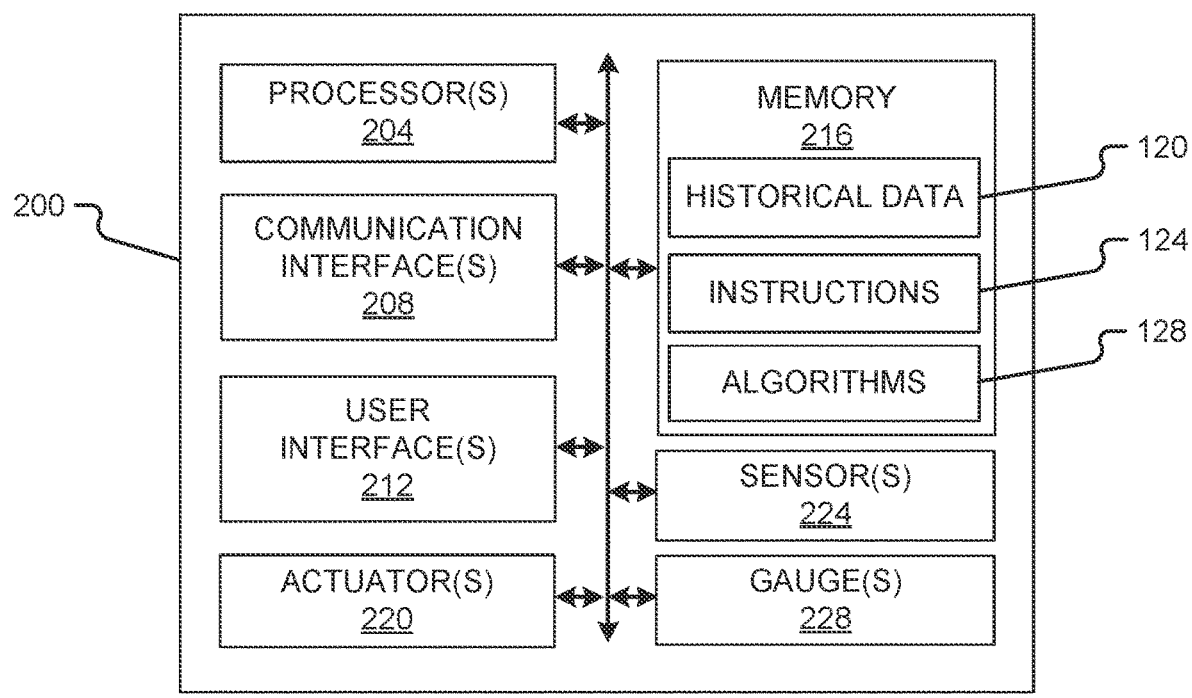
FIG. 2 is a block diagram of a device according to at least one embodiment of the present disclosure.

With reference now to FIG. 2, an interbody tool 200 according to some embodiments of the present disclosure may be used to determine an appropriate size and/or profile of an interbody implant. The interbody tool 200 comprises one or more processors 204, one or more communication interfaces 208, one or more user interfaces 212, at least one memory 216, one or more actuators 220, one or more sensors 224, and one or more gauges 228. Notwithstanding the layout of the interbody tool 200 as illustrated in FIG. 2, interbody tools according to other embodiments of the present disclosure may comprise more or fewer components than the interbody tool 200. In some embodiments, for example, the one or more actuators 220 may be configured to provide measurement information, in which embodiments the interbody tool 200 may not comprise separate gauges 228.

The one or more processors 204 may be the same as or similar to the at least one processor 104. For example, the one or more processors 204 of the interbody tool 200 may be any processor(s) identified or described herein or any similar processor(s). The one or more processors 204 may be configured to execute instructions 124 stored in the at least one memory 216, which instructions 124 may cause the one or more processors 204 to carry out one or more computing steps utilizing or based on data such as data received, for example, from the sensor(s) 224, from the gauge(s) 228, and/or from an external device such as a robot 140, a database 144, a cloud 148, and/or data stored in the memory 116 (e.g., historical data 120). The instructions 124 may also cause the one or more processors 204 to utilize one or more algorithms 128 stored in the memory 116. In some embodiments, the one or more processors 204 may be used to control the interbody tool 200 during a surgical procedure (e.g., by selectively activating and/or deactivating the actuator(s) 220 and/or receiving information or data from the sensor(s) 224 and/or the gauge(s) 228). The one or more processors 204 may also be used, in some embodiments, to control a robotic arm supporting the interbody tool 200.

The at least one communication interface 208 may be the same as or similar to the at least one communication interface 108. For example, the at least one communication interface 208 may be used for receiving a surgical plan, other planning data, and/or other information from an external source (such as a computing device 102, a robot 140, a database 144, a cloud 148, and/or a portable storage medium (e.g., a USB drive, a DVD, a CD)), and/or for transmitting sensor or gauge data (e.g., data received from the one or more sensors 224 and/or from the one or more gauges 228, respectively) or other information from the at least one processor 204 and/or the interbody tool 200 more generally to an external system or device (e.g., a computing device 102, another interbody tool 130, a robot 140, a database 144, a cloud 148, and/or a portable storage medium (e.g., a USB drive, a DVD, a CD)). The at least one communication interface 208 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 208 may be useful for enabling the interbody tool 200 to communicate with one or more other processors, whether to reduce the time needed to accomplish a computing-intensive task or for any other reason.

The at least one user interface 212 may be the same as or similar to the at least one user interface 112. For example, the at least one user interface 212 may be or comprise a keyboard, mouse, trackball, monitor, television, touchscreen, button, joystick, switch, lever, trigger, and/or any other device for receiving input and/or information from a user and/or for providing information to a user of the interbody tool 200. The at least one user interface 212 may be used, for example, to receive a user selection or other user input in connection with any step of any method described herein; to receive a user selection or other user input regarding one or more configurable settings of the interbody tool 200; to receive a user selection or other user input regarding how and/or where to store and/or transfer data received, modified, and/or generated by the interbody tool 200 (including the one or more sensors 224, the one or more gauges 228, and/or any other component of the interbody tool 200); and/or to display information (e.g., text, images) and/or to play a sound to a user based on data received, modified, and/or generated by the interbody tool 200. Notwithstanding the inclusion of the at least one user interface 212 in the interbody tool 200, the tool 200 may be configurable to operate automatically (e.g., under the control of the one or more processors 204, without any input via the at least one user interface 212 or otherwise) to carry out one or more, or all, of the steps of any method described herein.

Although the at least one user interface 212 is shown as part of the interbody tool 200, in some embodiments, the interbody tool 200 may utilize a user interface 212 that is housed separately from one or more remaining components of the interbody tool 200. In some embodiments, the user interface 212 may be located proximate one or more other components of the interbody tool 200, while in other embodiments, the user interface 212 may be located remotely from one or more other components of the interbody tool 200.

The at least one memory 216 may be the same as or similar to the memory 116. For example, the at least one memory 216 may be or comprise RAM, DRAM, SDRAM, other solid-state memory, any memory described herein, or any other tangible non-transitory memory for storing computer-readable data and/or instructions. The at least one memory 216 may store information or data useful for completing, for example, any step of the methods 300, 350, 400, or 500 described herein. The at least one memory 216 may store, for example, historical data 120, instructions 124, and/or algorithms 128, each of which is described in greater detail above. In some embodiments, the at least one memory 116 may also store one or more preoperative and/or other surgical plans; one or more images of one or more patients, including in particular of an anatomical feature of the one or more patients on which one or more surgical procedures is/are to be performed; data received from the at least one sensor 224 and/or from the at least one gauge 228; and/or other information useful in connection with the present disclosure.

The one or more actuators 220 may be the same as or similar to the one or more actuators 132 or any other actuators described herein. Similarly, the one or more sensors 224 may be the same as or similar to the one or more sensors 134 or any other sensors described herein, and the one or more gauges 228 may be the same as or similar to the one or more gauges 136 or any other gauges described herein.

Other embodiments of an interbody tool according to the present disclosure may comprise more or fewer components than shown in FIG. 2 with respect to the interbody tool 200. For example, in some embodiments, the actuators may also provide needed distance and/or other measurement information, such that separate gauges may be omitted.

Figure 3A:
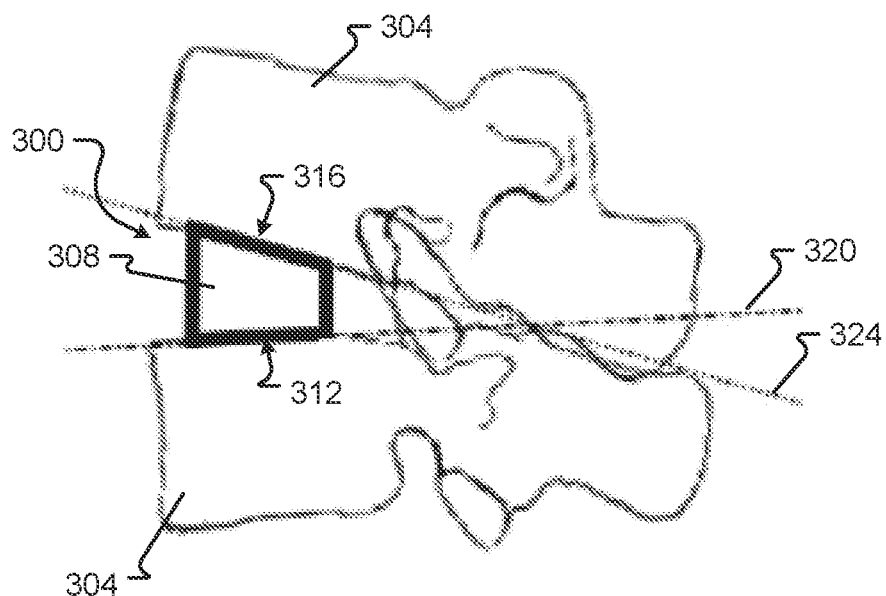
FIG. 3A illustrates a sagittal view of an interbody tool according to at least one embodiment of the present disclosure positioned in an interbody space.
Figure 3B:
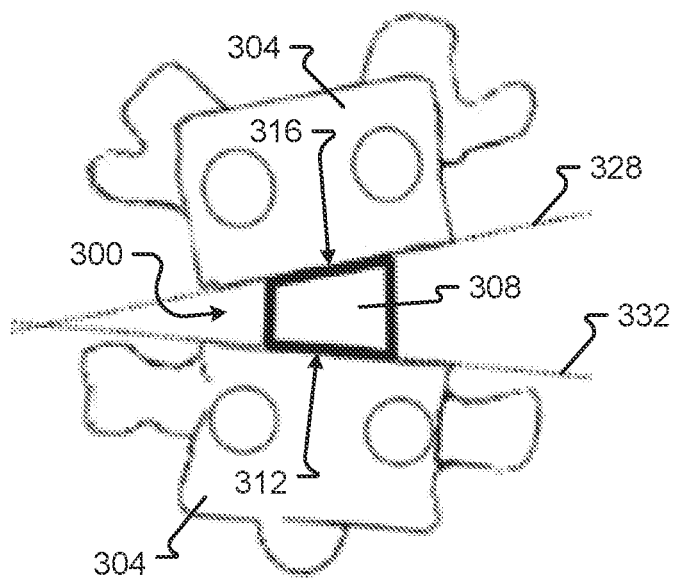
FIG. 3B illustrates an anterior view of an interbody tool positioned in an interbody space.

Each of FIGS. 3A-3B illustrate, from a sagittal perspective in FIG. 3A and an anterior perspective in FIG. 3B, an interbody space 300 with an interbody tool 308 positioned therein. Prior to insertion of an interbody tool such as the interbody tool 308 in an interbody space, the interbody space may be cleaned and otherwise prepared to receive an interbody implant, including by removal of a disc therein as well as any cartilage covering the vertebral surfaces. This ensures that any measurements and/or other information obtained using the interbody tool 308 will accurately reflect the characteristics of the interbody space at the time of implant insertion.

In each of FIGS. 3A-3B, the interbody tool 308 has been expanded so that a lower contact surface 312 is positioned against the cancellous bone of the lower vertebra 304, and an upper contact surface 316 is positioned against the cancellous bone of the upper vertebra 304. Using a plurality of gauges (not shown in FIG. 3A or 3B) of the interbody tool 308, a height of the interbody tool (corresponding to a distance between the upper and lower vertebra) at a plurality of points may be gauged or measured, so as to characterize the interbody space 300. For example, the interbody space 300 of FIG. 3A is taller proximate an anterior side thereof and shorter proximate a posterior side thereof. Similarly, the interbody space 300 of FIG. 3B is taller on one lateral side (the patient's left side, or the right side of FIG. 3B) and shorter on the opposite lateral side. Using the interbody tool 308, precise measurements of these differing heights may be obtained, and used to select an implant having an appropriate size and profile for the specific interbody space.

In some embodiments, the interbody tool 308 may be inserted into an interbody space such as the interbody space 300, and expanded using the one or more actuators thereof not just until the lower and upper contact surfaces (e.g., surfaces 312 and 316) are in contact with the respective adjacent vertebra, but until interbody tool 308 matches the size and profile of a predetermined interbody implant, or until the vertebrae (and, in some embodiments, the spine or a portion thereof) have been moved into a desired position. In the former instance, expansion of the interbody tool 308 until the tool 308 matches the size and profile of a predetermined interbody implant enables verification of the fit of the selected implant, including how the selected implant will affect the position of the vertebrae that define the interbody space and/or of the spine to which the vertebrae belong. In the latter instance, once the interbody tool 308 has been expanded until the vertebrae and/or the spine to which they belong have been moved into a desired position, the size and/or profile of the interbody tool 308 can be measured or otherwise determined, and used to select an appropriately sized interbody implant.

Figure 4A:
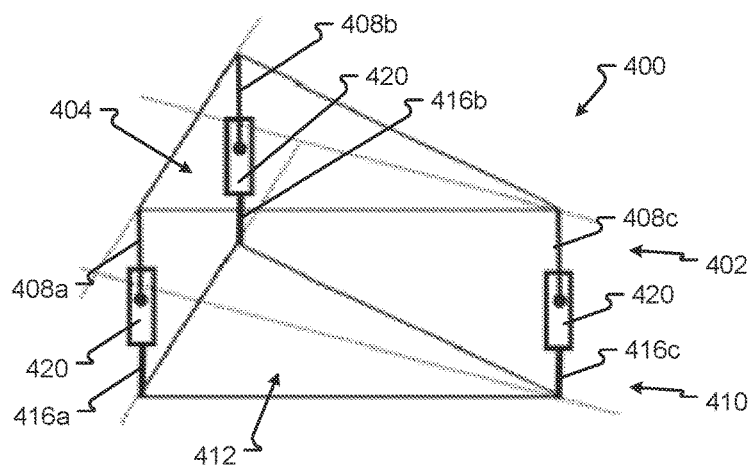
FIG. 4A illustrates an interbody tool according to at least one embodiment of the present disclosure in a first configuration.
Figure 4B:
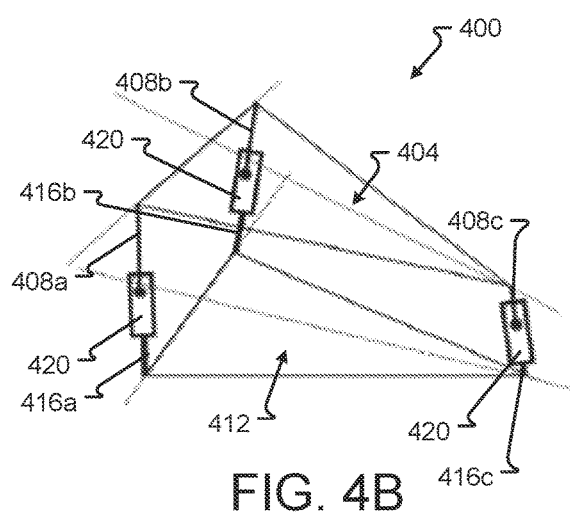
FIG. 4B illustrates the interbody tool of FIG. 4A in a second configuration.
Figure 4C:
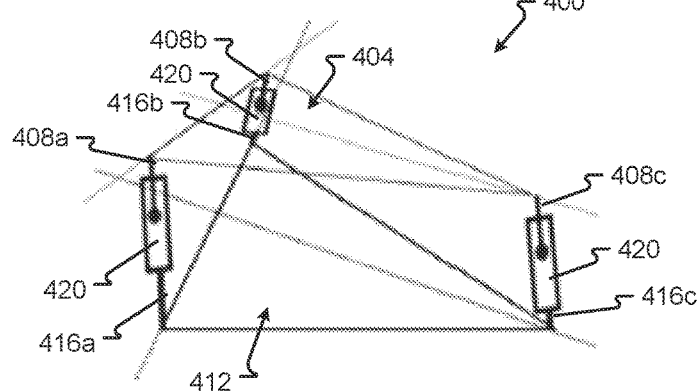
FIG. 4C illustrates the interbody tool of FIG. 4A in a third configuration.

FIGS. 4A to 4C illustrate an interbody implant 400 (shown in wireframe) according to one embodiment of the present disclosure in three different configurations. The interbody implant 400 comprises an upper portion 402 with an upper contact surface 404 and a plurality of upper legs 408a, 408b, and 408c extending therefrom. The interbody implant 400 also comprises a lower portion 410 with a lower contact surface 412 and a plurality of lower legs 416a, 416b, and 416c extending therefrom. Each of the plurality of upper legs 408 may be connected to the upper contact surface 404 via a mechanical hinge, a living hinge, or other joint, to allow the upper legs 408 to move relative to the upper contact surface 404. Similarly, each of the plurality of lower legs 416 may be connected to the lower contact surface 412 via a mechanical hinge, a living hinge, or other joint, to allow the lower legs 416 to move relative to the lower contact surface 412. The purpose of the hinged or otherwise jointed connection between each of the legs 408, 416 and the respective contact surface 404, 412 is to enable the legs 408, 416 to remain aligned with each other even when the upper contact surface 404 and lower contact surface 412 are not parallel. The upper legs 408 and the lower legs 416 may be manufactured from the same material as the upper and lower contact surfaces 404 and 412, respectively, or from a different material.

Each pair of upper and lower legs (e.g., upper leg 408a and lower leg 416a, upper leg 408b and lower leg 416b, and upper leg 408c and lower leg 416c) is connected via actuators 420, which are shown as hydraulic or pneumatic cylinders but which may be the same as or similar to (or replaced by) any other actuators described herein. The actuators 420 enable the upper legs 408 and the lower legs 416 to move relative to each other, such that a distance between the upper contact surface 404 and the lower contact surface 412 at each of the leg pairs 408 and 416 can be precisely adjusted.

Thus, in FIG. 4A, actuators 420 have been configured such that the upper contact surface 404 is substantially parallel to the lower contact surface 412. In FIG. 4B, the actuator 420 connecting the upper leg 408c and the lower leg 416c has been configured to shorten a distance between the upper contact surface 404 and the lower contact surface 412 proximate the legs 408c and 416c, such that the upper contact surface 404 and the lower contact surface 412 are sloped toward the legs 408c and 416c, respectively. And in FIG. 4C, the actuator 420 connecting the upper leg 408b and the lower leg 416b has been configured to shorten a distance between the upper contact surface 404 and the lower contact surface 412 proximate the legs 408b and 416b, such that the upper contact surface 404 and the lower contact surface 412 are sloped toward the legs 408b and 416b, respectively. The actuators 420 may be adjusted in any desirable manner to achieve various configurations and profiles of the interbody tool 400.

The upper contact surface 404 and the lower contact surface 412 may be made of stainless steel or any other stiff or rigid material capable of withstanding the forces and/or pressures required for the interbody tool 400 to be used for the purposes described herein. In some embodiments, the upper and lower contact surfaces 404 and 412 may have a contoured or rough surface to increase friction relative to the anatomical features that the surfaces will engage. In some embodiments, the upper and lower contact surfaces 404 and 412 may have a surface contour the same as or substantially similar to that of an interbody implant to be implanted in the interbody space based on information gathered using the interbody tool 400. In still other embodiments, the upper and lower contact surfaces 404 and 412 may be smooth. And, in some embodiments, the upper contact surface 404 may have a different surface finish or contour than the lower contact surface 412.

The interbody tool 400 may have closed sides in some embodiments and open sides in other embodiments. To ensure that the interbody tool 400 may be adjusted within a full range of motion of each actuator 420, embodiments of the interbody tool 400 having closed sides may have flexible or elastic sides. The flexible or elastic sides may be formed of any suitable material, including a biomaterial and/or a biocompatible material.

In some embodiments, the interbody tool 400 may comprise a frame comprising various rigid members to connect the various features thereof (e.g., as shown in FIGS. 4A-4C), which frame may be covered by a flexible or elastic covering or housing. In some embodiments, the flexible or elastic covering or housing may provide a sterile cover for non-sterile components within the flexible or elastic covering or housing. In embodiments comprising such a frame, the upper contact surface 404 may comprise the upper surfaces of the upper frame members, and the lower contact surface 412 may comprise the lower surfaces of the lower frame members. Thus, in such embodiments, the upper contact surface 404 and the lower contact surface 412 may not cover the entire top and bottom, respectively, of the interbody tool 400.

The actuators 420 may be configured to determine or otherwise measure a relative position of upper and lower legs 408 and 416 to which the actuators 420 are connected, such that separate gauges are not needed. In some embodiments of the present disclosure, however, the actuators 420 of the interbody tool 400 may be replaced by linear encoders or other distance- or height-measuring gauges, and one or more separate actuators (e.g., one or more inflatable balloons) may be positioned between the upper contact surface 404 and the lower contact surface 412 of the interbody tool 400, such that inflation of the one or more inflatable balloons pushes the upper and lower contact surfaces 404 and 412 away from each other. In such embodiments, the force exerted on the upper and lower contact surfaces 404 and 412 by the inflatable balloon or other actuator(s) from the inside of the interbody tool 400, and the force exerted on the upper and lower contact surfaces 404 and 412 from outside the interbody tool 400 by the anatomical features defining (in whole or in part) the interbody space, together cause the upper contact surface 404 and the lower contact surface 412 to align with the anatomical features in question (which may result, for example, in each of the different pairs of upper legs 408 and lower legs 416 having different heights, as shown, for example, in FIG. 4C).

Each contact surface 404, 412 of the interbody tool 400 of FIGS. 4A-4C comprises a triangle, with a leg 408 or 416 extending from each of the three corners of the triangle. The interbody tool 400 is adjustable in three degrees of freedom (pan, tilt, and height). In other embodiments of the present disclosure, each contact surface 404, 412 may comprise a shape other than a triangle, including a square, rectangle, or other polygon; a circle or ellipse; or any other shape. Also in other embodiments of the present disclosure, more or fewer than three legs may extend from each contact surface 404, 412, and the corresponding interbody tool may comprise more or fewer than three degrees of freedom.

Figure 5:
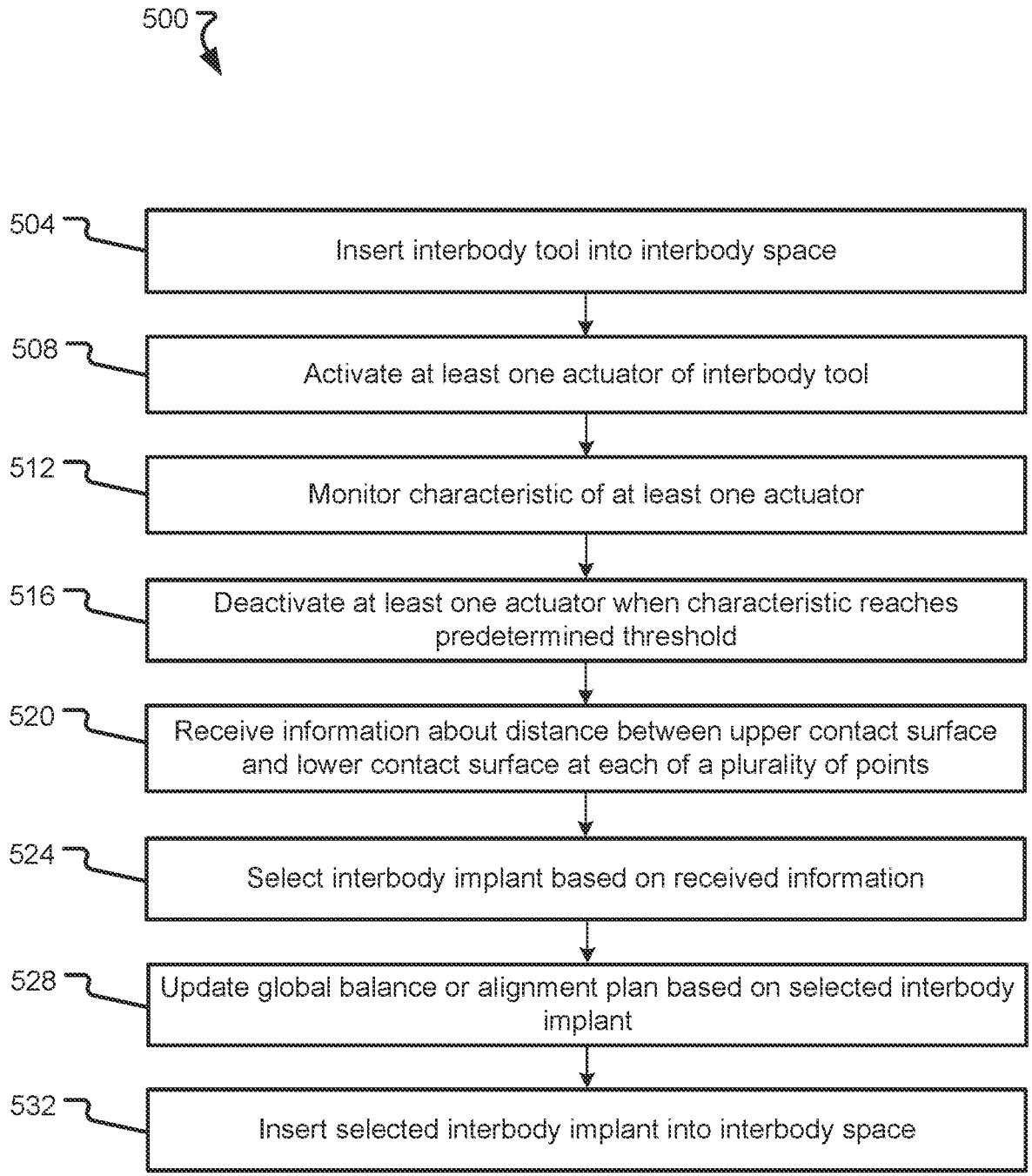
FIG. 5 is a flowchart of a method according to at least one embodiment of the present disclosure.

With reference now to FIG. 5, a method 500 for using an interbody tool according to embodiments of the present disclosure may be utilized during an interbody procedure. More specifically, although a surgical or other preoperative plan (e.g., a global alignment plan, a global balance plan) may comprise information about an interbody space in question—e.g., from a CT scan, MRI scan, or one or more X-ray images—a decision about the size and/or profile of an interbody implant requires additional information. This is particularly so given that the interbody space in the preoperative plan may not reflect the removal, during the procedure (and after creation of the preoperative plan), of a disc and/or other tissue from the interbody space. The method 500 may beneficially enable a surgeon or a robot (whether acting under the guidance of a surgeon or autonomously) to avoid the repeated insertion and removal of trials to determine a correct size and/or profile of an interbody implant. For a robot acting autonomously, repeated insertion and removal of trials may not provide adequate guidance to the robot regarding the best size and/or profile of an interbody implant; as a result, the method 500 may beneficially enable an autonomous robot to complete an interbody procedure where the robot would not otherwise be able to do so. Additionally, the method 500 may beneficially reduce the amount of trauma experienced by a patient during such repeated insertion and removal of trials, by inserting (and removing) the interbody tool only once.

The method 500 comprises inserting an interbody tool into an interbody space (step 504). The interbody tool may be the same as or similar to one or more of the interbody tool 130 of the system 100 as shown in FIG. 1, the interbody tool 200 as shown in FIG. 2, the interbody tool 308 as shown in FIGS. 3A and 3B, the interbody tool 400 as shown in FIGS. 4A-4C, or any other interbody tool according to embodiments of the present disclosure. The inserting may be accomplished manually by a surgeon holding the interbody tool with an interbody insertion device (e.g., the same device or type of device that may be used to insert an interbody implant) and/or with any other suitable tool, and placing the interbody tool into the interbody space of interest. In such embodiments, the surgeon may use a navigation system to facilitate proper placement of the interbody tool within the interbody space. The insertion may also be accomplished robotically or with robotic assistance, with a robot holding the interbody tool (whether directly in an end effector of a robotic arm of the robot, or at the end of a tool held by the end effector of the robotic arm of the robot). In some embodiments, the insertion may be accomplished autonomously, without any human input or guidance. Where a robotic arm is used to insert the interbody tool, the precise pose of the robotic arm at the time the robotic arm releases the interbody tool may be recorded, and used later in the method 500 to ensure that a selected interbody implant is inserted in precisely the same position.

Prior to insertion of the interbody tool in the interbody space, any tissue within the interbody space (e.g., a disc, cartilage) may have been removed and the interbody space may have been cleaned and otherwise prepared for insertion of the interbody tool and/or of an interbody implant.

During insertion of the interbody tool into the interbody space, the interbody tool may be placed in a minimum-size configuration. For example, the one or more actuators of the interbody tool may be moved (whether manually, by operation of the one or more actuators, or otherwise) into a minimum state of extension or expansion, so that the contact surfaces of the interbody tool are as close to each other as possible. Placement of the interbody tool into a minimum-size configuration prior to insertion thereof into the interbody space enables the interbody tool to fit through smaller incisions and/or other openings, and may thus enable smaller openings to be made, resulting in less tissue or other damage to the patient.

The method 500 also comprises activating at least one actuator of the interbody tool (step 508). The at least one actuator may be the same as or similar to an actuator 132, 220, 420, or any other actuator described herein. The at least one actuator may utilize mechanical force, electromagnetic force, hydraulic force, pneumatic force, or any other type of force to expand the interbody tool within the interbody space. Activation of the at least one actuator causes the at least one actuator to push the upper contact surface of the interbody tool away from the lower contact surface of the interbody tool. The activation may comprise, for example, providing electrical power to a motor that turns a screw jack within the interbody tool; providing electrical power to an electromagnet that generates a magnetic force that pushes the upper contact surface away from the lower contact surface; activating a hydraulic pump that increases a hydraulic pressure within an inflatable balloon within the interbody tool, and/or activating a pneumatic pump that increases an air pressure within an inflatable balloon within the interbody tool. One or more wires or hoses may connect the interbody tool to one or more power and/or pressure sources, and/or to a computing device such as the computing device 102, and/or to any other external (relative to the patient) components configured to control, provide information to, or receive information from the interbody tool.

The method 500 also comprises monitoring a characteristic of the at least one actuator (step 512). The characteristic may be a force exerted by or on the actuator, a pressure exerted by or existing within the actuator, a temperature of or within the actuator, or any other characteristic of the actuator. In some embodiments, more than one characteristic of the actuator may be measured. The monitoring may be accomplished or carried out by or using one or more appropriate sensors, such as a force sensor, a pressure sensor, a thermometer, and/or any other sensor. The sensor(s) may be the same as or similar to the sensor(s) 134, the sensor(s) 224, and/or any other sensors described herein. The sensor(s) may be configured to transmit raw data to a computing device such as the computing device 102 and/or to any other components of a system such as the system 100, or the sensor(s) may be configured to process raw data measured thereby and to transmit the processed data to a computing device such as the computing device 102 and/or to any other components of a system such as the system 100.

The method 500 also comprises deactivating the at least one actuator when the monitored characteristic reaches a predetermined threshold (step 516). For example, where the monitored characteristic is pressure, the at least one actuator may be deactivated when the monitored pressure reaches a predetermined threshold pressure. The predetermined threshold pressure may be a pressure beyond which the interbody tool may or will cause damage to the one or more anatomical features defining the interbody space in which the interbody tool has been inserted, and/or beyond which the interbody tool may or will otherwise harm the patient. For example, where the at least one actuator comprises a screw jack, and the interbody tool is inserted into an interbody space between two vertebrae, the predetermined threshold pressure may be a pressure sufficiently high enough to cause desired movement of a spine comprising the two vertebrae, but not so large that one or both of the vertebrae will fracture, or that the spine will be otherwise damaged. In some embodiments, the predetermined threshold pressure may be a design limit of the interbody tool, the at least one actuator, or any other component of the interbody tool. For example, if the at least one actuator comprises an inflatable balloon, the predetermined threshold pressure may be determined by applying a desired margin of safety to the pressure at which the inflatable balloon will burst.

The predetermined threshold, in some embodiments, may be based on historical data such as the historical data 120. For example, historical data 120 may be available for a plurality of procedures in which an interbody tool such as any interbody tool described herein was used to characterize an interbody space. Such historical data 120 may comprise information about the size and/or profile of the interbody space as determined using the interbody too; information about the patient and any condition(s) affecting the patient, including curvature of the spine or other spinal conditions; information about the maximum force, pressure, and/or other measured characteristic(s) that occurred during, or resulted from, use of the interbody tool; and/or information about patient outcomes, including fusion rates, amount or degree of correction of excess spinal curvature, and so forth. The historical data 120 may comprise any other information described herein. Using a machine learning algorithm from among the algorithms 128, or any other algorithm(s), such historical data 120 may be analyzed and used to identify (together with information about a particular patient for which an interbody procedure will be performed, including, for example, information about the amount of correction needed according to a global alignment plan) a patient-specific predetermined threshold for the measured characteristic. Such historical data may also be used to assist with other aspects of the preoperative planning process.

In some embodiments, the method 500 may comprise monitoring a characteristic of a patient, whether in addition to or instead of monitoring a characteristic of the at least one actuator. For example, where the interbody tool is used to determine the size and/or profile of an interbody implant needed to correct an undesired condition of an anatomical feature (e.g., to correct lordosis or kyphosis of a spine), the method 500 may comprise monitoring the condition (e.g., the curvature) of the anatomical feature (e.g., the spine) as the at least one actuator expands the interbody tool until the anatomical feature reaches a desired or acceptable degree of correction (e.g., to determine at which point the curvature of the spine is corrected or reaches a desired or acceptable degree of curvature). Thus, in some embodiments, the predetermined threshold may be or comprise a threshold relating to a physical condition of the patient. The at least one actuator may then be deactivated, with the method 500 continuing with the step 520.

In some embodiments, the predetermined threshold may comprise a plurality of predetermined thresholds, each relating to a different characteristic. In such embodiments, the method 500 may comprise monitoring a plurality of characteristics, and deactivating the at least one actuator when at least one of the monitored characteristics reaches a corresponding predetermined threshold.

The method 500 further comprises receiving information about or corresponding to a distance between an upper contact surface and a lower contact surface at each of a plurality of points (step 520). The distance may be measured in millimeters or any other suitable units. In some embodiments, the distance may be between, for example, three millimeters and twenty-four millimeters, or between five millimeters and twenty millimeters, or between six millimeters and eighteen millimeters. The distance may be measured by one or more gauges such as the gauges 136 or 228 described above, or by any other gauge or gauges. The plurality of points may correspond to points where legs such as the legs 408, 416 extend from upper and lower contact surfaces, respectively, of the interbody tool. In some embodiments, the distance may be measured directly, while in other embodiments, the distance may be measured indirectly (e.g., by measuring a position of an upper leg such as an upper leg 408 from a corresponding lower leg such as the lower leg 416). In embodiments where the distance is measured indirectly, the one or more gauges may calculate the actual distance based on the indirect measurements (e.g., by adding or subtracting a distance between an end of an upper leg and an end of a lower leg from a known distance between the upper and lower contact surfaces when the upper and lower legs are placed end to end, depending on whether the upper and lower legs are not overlapping or are overlapping, respectively). Alternatively, the one or more gauges may provide the indirect measurements to a computing device 102 or other external device, which may then calculate the actual distance between the contact surfaces at each of the plurality of points.

Although not shown in FIG. 5, the method 500 may comprise returning the interbody tool to a minimum-size configuration and removing the interbody tool from the interbody space. The removing may be accomplished in the same or a similar manner as the inserting described above. Thus, for example, the removing may be accomplished manually, robotically or with robotic assistance, and/or fully autonomously.

The method 500 further comprises selecting an interbody implant based on the received information (step 524). Based on the distance information received in the step 520 (whether such information is raw information that must be calculated to obtain an actual distance, or such information provides the actual distance), a size and profile of an interbody implant may be selected. The selecting may comprise identifying an implant that has a size and profile most similar to the size and profile of the interbody tool as measured by the one or more gauges (or as determined based on information received from the one or more gauges). The selecting may be done by a surgeon, or the selecting may be done automatically (e.g., without human input). For example, the selecting may comprise inputting size and profile information of the interbody tool (as measured by or determined based on information received from the one or more gauges) into a look-up table (which may be stored, for example, in a database such as the database 144, or in a memory such as the memory 116 or 216) that contains information about available interbody implants. In this way, the interbody implant having the closest size and profile to those obtained using the interbody tool may be automatically identified. To ensure that the interbody implant is not too large, the look-up table may return an interbody implant that most closely matches the size and profile determined using the interbody tool, but that has critical dimensions (e.g., dimensions in the directions that affect the fit of the implant within the interbody space) that are equal to or less than any corresponding critical dimensions determined using the interbody tool.

Where an implant that closely matches the needed size and/or profile determined using the interbody tool is not available, a custom implant may be made. The custom implant may be made by modifying an existing implant, or by cutting an implant blank to an appropriate size and/or profile, or using an additive manufacturing process (e.g., a 3D printer) to make the custom implant from scratch.

The method 500 also comprises updating a global balance or alignment plan based on the selected interbody implant (step 528). A global balance or alignment plan may be updated to reflect use of the selected implant, and/or to reflect other changes required as a result of the selected implant. For example, if a global balance or alignment plan calls for a forty-degree lordotic angle, then the lordotic angle of the patient's spine may be monitored during activation of the at least one actuator, and the at least one actuator may be deactivated when the lordotic angle reaches forty degrees (e.g., during the step 516). The interbody implant selected during the step 520 may be an interbody implant having the size and/or profile of the interbody tool when the interbody tool was configured to cause the lordotic angle of the patient's spine to reach forty degrees. In some embodiments, this may comprise removing or updating information in the global balance or alignment plan about a size and/or profile of an implant that was planned to be used, but that is determined to not be the correct size and/or profile as a result of use of the interbody tool.

Relatedly, if a global balance or alignment plan calls for a forty-degree lordotic angle (for example), but use of the interbody tool as described herein indicates that an appropriate, recommended, or maximum size and/or profile of an implant for the interbody space in question will be insufficient to achieve the desired forty-degree lordotic angle, then the global balance or alignment plan may be amended to include an additional implant at an adjacent spinal level to achieve the desired lordotic angle (or, where an additional implant at an adjacent spinal level is already provided for in the global alignment plan, to adjust a size and/or profile of the additional implant so as to achieve the desired lordotic angle).

The method 500 also comprises inserting the selected interbody implant into the interbody space (step 532). The inserting may be accomplished in the same way as in the step 504. For example, the inserting may be accomplished manually by a surgeon holding the interbody implant with an interbody insertion device and/or with any other suitable tool, and placing the interbody implant into the interbody space of interest. The insertion may also be accomplished robotically or with robotic assistance, with a robot holding the interbody implant (whether directly in an end effector of a robotic arm of the robot, or at the end of a tool held by the end effector of the robotic arm of the robot). In some embodiments, the insertion may be accomplished autonomously, without any human input or guidance. Where a robotic arm was used to insert the interbody tool, and the precise pose of the robotic arm at the time the robotic arm released the interbody tool was recorded, the recorded pose may be utilized by the robot to ensure that a selected interbody implant is inserted in precisely the same position.

As may be appreciated based on the foregoing disclosure, the present disclosure encompasses methods with fewer than all of the steps identified in FIG. 5 (and the corresponding description of the method 500), as well as methods that include additional steps beyond those identified in FIG. 5 (and the corresponding description of the method 500). Any component or element referenced in the foregoing description of the method 500 may be the same as or similar to any corresponding component or element described herein.

One or more aspects of the present disclosure may be the same as or similar to corresponding aspects described in U.S. patent application Ser. No. 16/903,696, filed by the same Applicant as the present application on Jun. 17, 2020, and entitled "Torque Sensor with Decision Support and Related Systems and Methods," the entirety of which is hereby incorporated herein by reference.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An interbody measurement system comprising:
   an interbody tool comprising:
      an upper portion comprising an upper contact surface and a plurality of upper legs;
      a lower portion comprising a lower contact surface and a plurality of lower legs, each of the lower legs moveably connected to one of the upper legs;
      a plurality of actuators configured to selectively adjust a distance between the upper contact surface and the lower contact surface, each actuator connecting a corresponding upper leg of the plurality of upper legs and a corresponding lower leg of the plurality of lower legs; and
      at least one sensor for measuring a characteristic of at least one actuator in the plurality of actuators;
   a processor; and
   a memory storing data for processing by the processor, the data, when processed, causes the processor to:
      activate the plurality of actuators;
      receive data corresponding to the characteristic from the at least one sensor;
      determine whether to de-activate the plurality of actuators based on the data corresponding to the characteristic;
      receive information about a distance between the upper contact surface and the lower contact surface;
      identifying an implant based on the information about the distance between the upper contact surface and the lower contact surface at each of a plurality of points; and
      update at least one parameter of a global alignment plan based on the identified implant.

2. The interbody measurement system of claim 1, wherein the interbody tool further comprises a plurality of gauges positioned at the plurality of points between the upper contact surface and the lower contact surface, and wherein the information about the distance between the upper contact surface and the lower contact surface is received from the plurality of gauges at each of the plurality of points.

3. The interbody measurement system of claim 2, wherein each of the plurality of gauges comprises at least one of an encoder and an optical distance sensor.

4. The interbody measurement system of claim 1, wherein the memory stores further data for processing by the processor that, when processed, causes the processor to:
   cause a robot to insert the identified implant into an interbody space.

5. The interbody measurement system of claim 1, wherein the characteristic comprises a force, and memory stores further data for processing by the processor that, when processed, causes the processor to:
   deactivate the at least one actuator when the force, as measured by the at least one sensor, reaches a predetermined threshold.

6. The interbody measurement system of claim 1, wherein each actuator of the plurality of actuators comprises at least one of a scissor jack, a pneumatic actuator, a hydraulic actuator, or one or more electromagnets.

7. The interbody measurement system of claim 1, wherein each actuator of the plurality of actuators comprises a plurality of independently operable hydraulic actuators and the at least one sensor comprises a plurality of pressure sensors.

8. An interbody measurement system comprising:
   an interbody tool comprising:
      an upper portion comprising an upper contact surface and a plurality of upper legs;
      a lower portion comprising a lower contact surface and a plurality of lower legs, each of the lower legs moveably connected to one of the upper legs;
      a plurality of gauges positioned at a plurality of points between the upper contact surface and the lower contact surface;
      a plurality of actuators configured to selectively adjust a distance between the upper contact surface and the lower contact surface, each actuator connecting a corresponding upper leg of the plurality of upper legs and a corresponding lower leg of the plurality of lower legs; and
      at least one sensor for measuring a characteristic of at least one actuator in the plurality of actuators;
   a processor; and
   a memory storing data for processing by the processor, the data, when processed, causes the processor to:
      receive, from the plurality of gauges, information about a distance between the upper contact surface and the lower contact surface at each of the plurality of points;
      identify an implant based on the information about the distance between the upper contact surface and the lower contact surface at each of the plurality of points; and update at least one parameter of a global alignment plan based on the identified implant.

9. The interbody measurement system of claim 8, wherein the memory stores further data for processing by the processor that, when processed, causes the processor to:
receive data corresponding to the characteristic from the at least one sensor; and
determine whether to de-activate the plurality of actuators based on the data corresponding to the characteristic.

10. The interbody measurement system of claim 8, wherein the characteristic comprises a force, and memory stores further data for processing by the processor that, when processed, causes the processor to:
deactivate the plurality of actuators when the force, as measured by the at least one sensor, reaches a predetermined threshold.

11. The interbody measurement system of claim 8, wherein the memory stores further data for processing by the processor that, when processed, causes the processor to:
cause a robot to insert the identified implant into an interbody space.

12. The interbody measurement system of claim 8, wherein each of the plurality of gauges comprises at least one of an encoder or an optical distance sensor.

13. The interbody measurement system of claim 8, wherein each of the plurality of actuators comprises at least one of a scissor jack, a pneumatic actuator, a hydraulic actuator, or one or more electromagnets.

14. The interbody measurement system of claim 8, wherein the plurality of actuators comprises a plurality of independently operable hydraulic actuators and the at least one sensor comprises a plurality of pressure sensors.

15. An interbody measurement system comprising:
an interbody tool comprising:
an upper portion comprising an upper contact surface and a plurality of upper legs;
a lower portion comprising a lower contact surface and a plurality of lower legs, each of the lower legs moveably connected to one of the upper legs;
a plurality of actuators configured to selectively adjust a distance between the upper contact surface and the lower contact surface, each actuator connecting a corresponding upper leg of the plurality of upper legs and a corresponding lower leg of the plurality of lower legs; and
at least one sensor for measuring a force exerted by at least one actuator in the plurality of actuators;
a processor; and
a memory storing data for processing by the processor, the data, when processed, causes the processor to:
activate the plurality of actuators;
deactivate the plurality of actuators when the force, as measured by the at least one sensor, reaches a predetermined threshold;
receive information about a distance between the upper contact surface and the lower contact surface;
identify an implant based on the information about the distance between the upper contact surface and the lower contact surface at each of a plurality of points; and
update at least one parameter of a global alignment plan based on the identified implant.

16. The interbody measurement system of claim 15, wherein the interbody tool further comprises a plurality of gauges positioned at the plurality of points between the upper contact surface and the lower contact surface, and the memory stores further data for processing by the processor that, when processed, causes the processor to:
receive, from the plurality of gauges, the information about the distance between the upper contact surface and the lower contact surface at each of the plurality of points.

17. The interbody measurement system of claim 15, wherein the memory stores further data for processing by the processor that, when processed, causes the processor to:
cause a robot to insert the identified implant into an interbody space.

18. The interbody measurement system of claim 15, wherein the plurality of actuators comprises a plurality of independently operable hydraulic actuators and the at least one sensor comprises a plurality of pressure sensors.

* * * * *